(12) United States Patent
Gminder et al.

(10) Patent No.: US 6,699,185 B2
(45) Date of Patent: Mar. 2, 2004

(54) MEDICAL ENDOSCOPIC INSTRUMENT

(75) Inventors: Frank Gminder, Trossingen (DE); Horst Dittrich, Immendingen (DE); Frank Doll, Dürbheim (DE)

(73) Assignee: Karl Storz GmbH & Co. KG (DE)

( * ) Notice: Subject to any disclaimer, the term of this patent is extended or adjusted under 35 U.S.C. 154(b) by 23 days.

(21) Appl. No.: 09/950,034

(22) Filed: Sep. 10, 2001

(65) Prior Publication Data

US 2002/0007109 A1 Jan. 17, 2002

Related U.S. Application Data

(63) Continuation of application No. PCT/EP00/01316, filed on Feb. 18, 2000.

(30) Foreign Application Priority Data

Mar. 9, 1999 (DE) .......................................... 199 10 295

(51) Int. Cl.$^7$ ................................................. A61B 1/12
(52) U.S. Cl. ........................ 600/157; 600/156; 600/158; 606/46
(58) Field of Search .............................. 600/157, 156, 600/158; 606/46

(56) References Cited

U.S. PATENT DOCUMENTS

| | | | | | |
|---|---|---|---|---|---|
| 3,835,841 A | * | 9/1974 | Terada | .......................... | 600/157 |
| 4,436,087 A | * | 3/1984 | Ouchi | .......................... | 600/157 |
| 4,726,370 A | * | 2/1988 | Karasawa et al. | ............. | 606/46 |
| 4,878,893 A | * | 11/1989 | Chin | .......................... | 600/156 |
| 5,386,817 A | * | 2/1995 | Jones | .......................... | 600/158 |
| 5,518,502 A | * | 5/1996 | Kaplan et al. | ............... | 600/157 |
| 5,688,222 A | | 11/1997 | Hluchy | ........................ | 600/156 |
| 6,176,825 B1 | * | 1/2001 | Chin et al. | ................... | 600/157 |

FOREIGN PATENT DOCUMENTS

| | | |
|---|---|---|
| DE | 86 21 769.0 | 5/1987 |
| DE | 195 20 277 C1 | 11/1996 |
| DE | 199 10 295 A1 | 9/1999 |
| EP | 0 664 101 A1 | 1/1994 |
| FR | 1.548.389 | 8/1967 |
| WO | WO 92/20274 | 5/1992 |
| WO | WO 96/39915 | 6/1995 |
| WO | WO 98/43531 | 4/1997 |

OTHER PUBLICATIONS

Karl Storz Resektoskop 4/96 1 page.
Richard Wold G.m.b.H. Endoskop mit Spuleinrichung dated Jul. 20, 1967 5 pages.

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

An endoscopic instrument is provided comprising a shaft having an endoscope optical system arranged therein, which has a distal front face. The instrument also comprises a working element arranged in the shaft. The shaft provides for the supply of an irrigation fluid. Flow-influencing means are provided, such that the irrigation fluid reaches in front of the front face of the endoscope optical system and can eliminate contaminations, which obstruct the view through the endoscope optics.

11 Claims, 3 Drawing Sheets

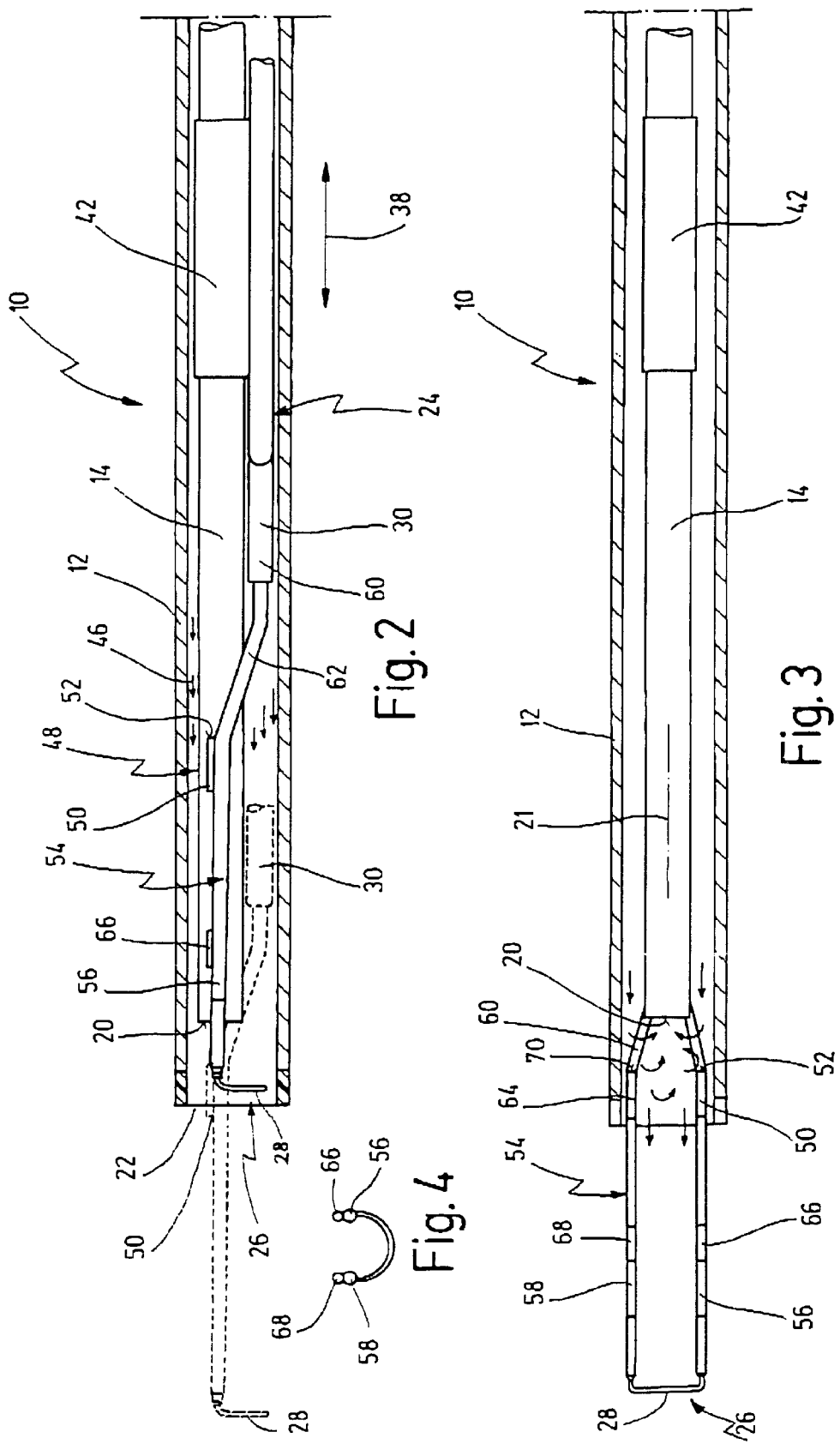

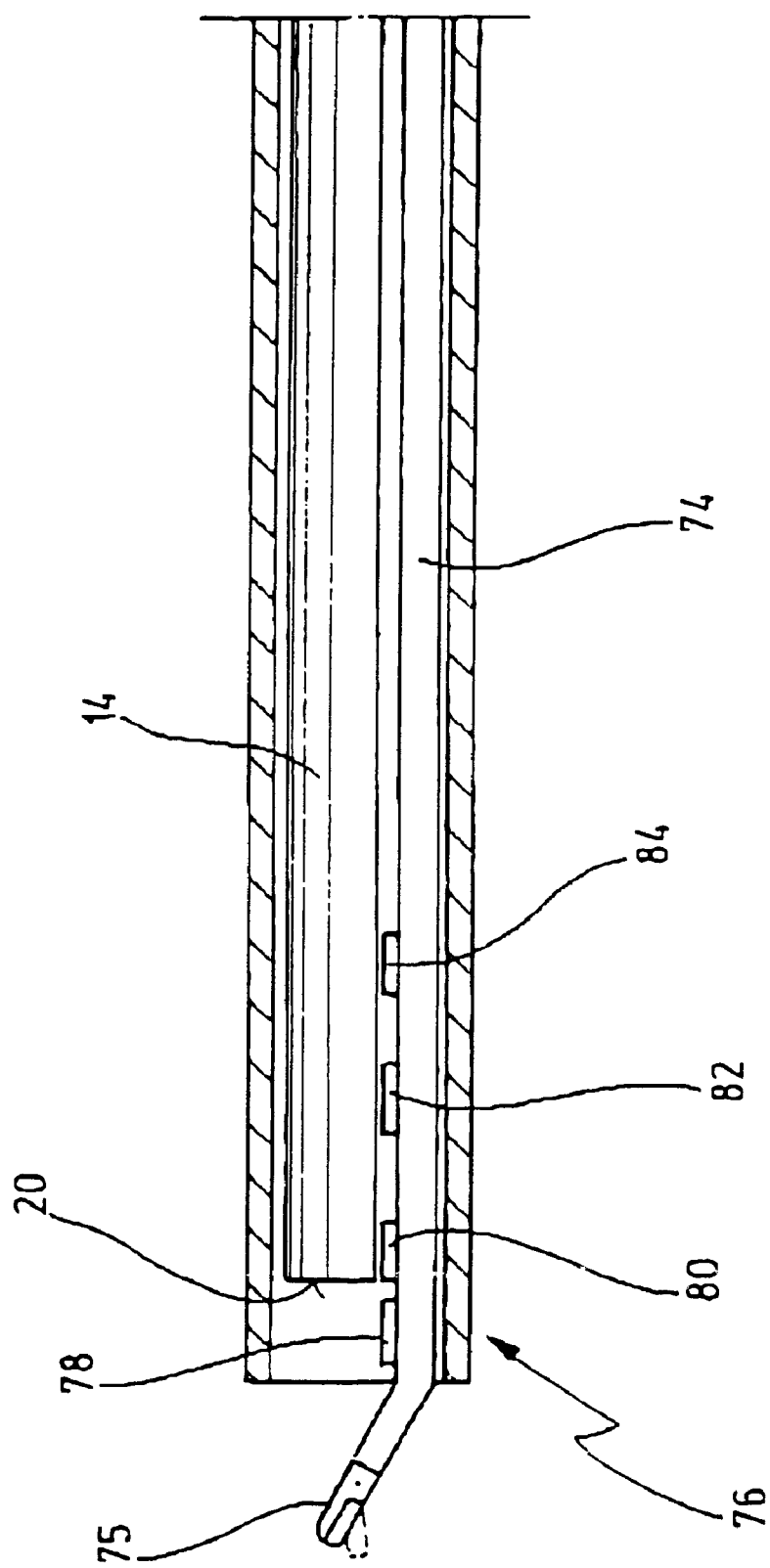

MEDICAL ENDOSCOPIC INSTRUMENT

The present application is a continuation of International Patent Application PCT/EP00/01316 filed on Feb. 18, 2000, which designates the United States and which claims priority of German patent application 199 10 295 filed on Mar. 9, 1999

BACKGROUND OF THE INVENTION

The invention relates to a medical or technical endoscopic instrument, comprising a shaft having an endoscope optical system arranged therein, which comprises a distal front face, and a working element also arranged in the shaft, wherein further the shaft serves to supply an irrigation fluid into an operation or application area.

A medical instrument of this kind is known from document DE-C-195 20 277.

By means of a medical instrument of the type mentioned at the outset, tissue in the human or animal body is treated with the working element, for example is removed, grasped and/or coagulated in minimally invasive surgery under endoscopic control with the endoscope optical system.

For treating tissue, a working element is used with at least one tool which is configured as a purely mechanically cutting tool, for example in the form of forceps jaws, or as an electrode supplied with high frequency current, with which tissue can be removed or cut or coagulated due to the action of high frequency current.

Such an instrument for medical purposes is known for example from the German catalogue of the firm Karl Storz GmbH & Co., Tuttlingen, "Karl Storz-Endoskope", Vol. Urology, page RES-SC 6 A, Edition 1995.

The instrument known from the German catalogue mentioned at the outset is a resectoscope, where the various working elements having cutting electrodes, coagulation electrodes or curettes can be inserted with which the corresponding treatment can be carried out. The invention however is not limited to a resectoscope.

Endoscopic instruments of this type are also known for technical purposes, which are used in difficultly accessible spaces in machines, motors or the like.

Since bleeding naturally occurs when removing tissue, such instruments provide for the introduction of an irrigation fluid through the shaft into the operation area to irrigate away the blood which obstructs the view. The irrigation fluid is passed through the shaft from the proximal end to the distal end, where it exits from the distal end to irrigate the operation area in the region of the tool. Normally, an excess cross-section remaining in the shaft when the endoscopic optical system and the working element are inserted is usable as an irrigation cross-section. The irrigation fluid therefore flows in the shaft along the endoscope optical system and passes its front face.

The problem results with the irrigation fluid running along the endoscope optical system, that a dead space of flow is formed distally in front of the front face of the optical system, which is the light emission and the light inlet end of the endoscope optical system. This means that the irrigation fluid during irrigation does not reach distally in front of the front face of the optical system. Rather, blood and pieces of tissue can collect there, which are not reached by the irrigation fluid and are not washed away. However, the blood and tissue pieces collecting in front of the front face are non-transparent and thus obstruct visual control with the endoscope optical system. The problem of a dead space in the flow arises particularly for optical systems with a straight-forward view or oblique-forward view, whose front faces are nearly perpendicular to the flow direction of the irrigation fluid, i.e. when a perpendicular line to the front face makes an angle of about 0° to about 20° with respect to the flow direction.

The additional problem arises in instruments for treating tissue with high frequency current that small gas bubbles form when treating the tissue with high frequency current. These collect in the dead space of flow in front of the distal front face of the optical system and adhere to the front face and are not caught by the irrigation fluid and washed away due to the formation of the dead space of flow.

The instrument known from document DE-C-195 20 277 mentioned at the outset comprises a shaft, an endoscope optical system received therein and a working element also received in the shaft. In the remaining space between the shaft, the endoscope optical system and the working element, an irrigation fluid is conducted from the proximal end to the distal end. Flow-influencing means are provided for the purpose that the irrigation fluid reaches in front of the front face of the endoscope optical system. The flow-influencing means comprises an opening in the shaft and an outer shaft arranged about the shaft and spaced therefrom, wherein in the space between the outer shaft and the shaft, a vacuum is applied. The irrigation fluid conducted through the shaft to the distal end is sucked through the opening into the space between the outer shaft and the shaft, whereby the irrigation fluid is conducted along the front face of the endoscope optical system.

The object of the present invention is to provide an instrument of the type mentioned at the outset in which the handling of the instrument is improved.

SUMMARY OF THE INVENTION

According to the present invention, this object is achieved with respect to the instrument mentioned at the outset by an endoscopic instrument, comprising a shaft, an endoscope optical system arranged in said shaft, said endoscope optical system having a distal front face, and a working element arranged in said shaft, wherein said shaft serves to supply an irrigation fluid into an operation or application area, wherein flow-influencing means are provided such that said irrigation fluid reaches in front of said front face of said endoscope optical system, and wherein said flow-influencing means are provided on said working element.

The instrument according to the present invention, thus, provides suitable means for influencing the flow of irrigation fluid in the region of the front face such that at least a portion of the irrigation fluid is deflected in front of the front face and a fluid flow occurs in the dead space of flow formed in conventional instruments in front of the front face. Thus, the blood, tissue pieces and optionally gas bubbles which can collect in front of the front face and obstruct the view are caught by the irrigation fluid and washed away. The invention avoids the collection of non-transparent fluids or tissue pieces, in particular for endoscope optical systems whose front face is disposed perpendicularly or nearly perpendicularly to the flow direction and where a dead space of flow forms to greater extent. The flow-influencing means can be configured and arranged such that the otherwise substantially laminar flow in the region of the end face of the optics is converted into a turbulent flow and/or the flow direction of the flushing fluid can be deflected such that a flow component along the front face of the optical system is formed. In both cases, it is guaranteed that the front face is sufficiently irrigated with the irrigation fluid. According to the invention, the flow-influencing means are provided on the working element. The advantage is that the flow-influencing means can be configured and positioned such that they do not obstruct the view. Since the working elements are often arranged to be axially shiftable relative to the endoscope optical system, this configuration opens up the very advantageous possibility of providing different flow conditions by moving the working element back and forth to efficiently deflect the flushing fluid in front of the front face.

The object underlying the invention is thus completely achieved.

In a preferred embodiment, the flow-influencing means are configured as flow obstructions which cause a swirling of the irrigation fluid in front of the front face of the optical system.

The advantage is that a swirling of the irrigation fluid in front of the front face of the endoscope optical system effectively causes a mixing of the irrigation fluid with the blood collected in front of the front face and results in a very effective removal of adhering gas bubbles or pieces of tissue.

In a further preferred embodiment, the flow-influencing means are configured as flow deflection means which generate a flow component along the front face of the endoscope optical system.

This feature also is suitable for preventing a dead space of flow in front of the front face of the endoscope optical system, wherein the irrigation fluid in the region of the front face is deflected from its original, substantially axially directed flow direction, such that at least a partial flow is formed along the front face and the front face is thus effectively irrigated.

In a further preferred embodiment, the flow-influencing means comprise at least one flow element which comprises a surface against which the irrigation fluid flows, and which is inclined or runs transversely with respect to the flow direction.

The inclined or transversed surface, against which the fluid flows and which projects from the working element, leads to a swirling of the irrigation fluid in the region of the front face of the endoscope optical system in an advantageously constructively simple manner. The flow element or flow elements can be simply attached to the working element as an additional part, for example in the form of small rods, small plates, guide plates or the like.

The surface is preferably flat or has a concave curvature directed to an axis of the endoscope optical system.

When the surface is flat and inclined or transverse to the flow direction, this surface substantially acts as an impact surface leading to a swirling of the irrigation fluid. A deflection of the flow direction can be achieved with a concave curvature of the surface, such that the irrigation fluid flows along the front face of the optics.

In a further preferred embodiment, several flow elements are arranged axially and/or circumferentially distributed on the working element.

The feature has the advantage that a precise influence of the flow of irrigation fluid can be enhanced with several flow elements arranged and distributed on the working element. When the working element is axially movable, a further advantage is that sufficient irrigation of the space in front of the front face is guaranteed at different axial working positions of the working element.

In a further preferred embodiment, the working element has a forked section in a distal region, wherein two legs of the forked section run axially along the sides of the endoscope optical system and run together at a proximal unitary section, which extends axially adjacent to the endoscope optical system. The working element comprises a bend in the transition region from the forked section to the unitary section, which lies axially in the region of the front face of the optics in at least one axial working position of the working element.

Such a bend is provided in conventional working elements of this type, which normally serve as an electrode support for an electrode supplied with high frequency current. However, in these known working elements, the bend is proximally behind the front face of the endoscope optical system in every axial position of the working element relative to the endoscope optical system. In contrast, according to the configuration of the present invention, the bend of the working element, which is located in the approximately V-shaped transition region between the forked section and the unitary section, is configured such that the bend is located axially in the region of the front face of the optics at least in one position of the working element. Thus, the bend can advantageously be used as a flow-influencing measure for precisely affecting the flow of the irrigation fluid in the region distally in front of the front face of the endoscope optical system.

In a further preferred embodiment, the working element is axially shiftable relative to the endoscope optical system.

The advantage is that the intended influence on the irrigation fluid flow can be additionally enhanced by an axial back and forth movement.

In a further preferred embodiment, the working element is an electrode carrier, and the at least one tool is an electrode supplyable with HF current.

As already mentioned at the outset, the additional problem arises with high frequency instruments that the effect of high frequency power produces gas bubbles which adhere to the front face of the endoscope optical system. It is now advantageously achieved, through the flow-influencing means provided in the present invention, that the gas bubbles can also be washed away from the front face of the endoscope optical system through the intended influence on the irrigation fluid flow.

However, it is also preferred when the working element has a shaft with a mechanically acting tool. Blood can also collect in front of the front face of the endoscope optical system in conventional instruments which do not use high frequency power, because a dead space of flow forms there. This problem is also effectively eliminated by the invention, also for purely mechanical instruments through a precise influence on the irrigation fluid flow by flow-influencing means.

Further advantages can be taken from the following description and the appended drawings.

It will be understood that the above-mentioned features and those to be discussed below are applicable not only in the given combinations, but may also be used in other combinations or taken alone without departing from the scope of the present invention.

Selected embodiments of the invention are illustrated in the drawings and will be described in detail in the following.

BRIEF DESCRIPTION OF THE DRAWINGS

FIG. 2 shows a partial cross-section through the distal region of the instrument in FIG. 1 in side view in enlarged scale.

FIG. 3 shows a partial cross-section through the distal region of the instrument in FIG. 1 in plan view in enlarged scale.

FIG. 4 shows a front view of the distal end of the working element of the instrument.

FIG. 5 shows a partial cross-section corresponding to FIG. 2 through the instrument in FIG. 1, where the working element of FIGS. 2 to 4 is replaced by a mechanical working element.

DETAILED DESCRIPTION OF THE DRAWINGS

Figure 1:
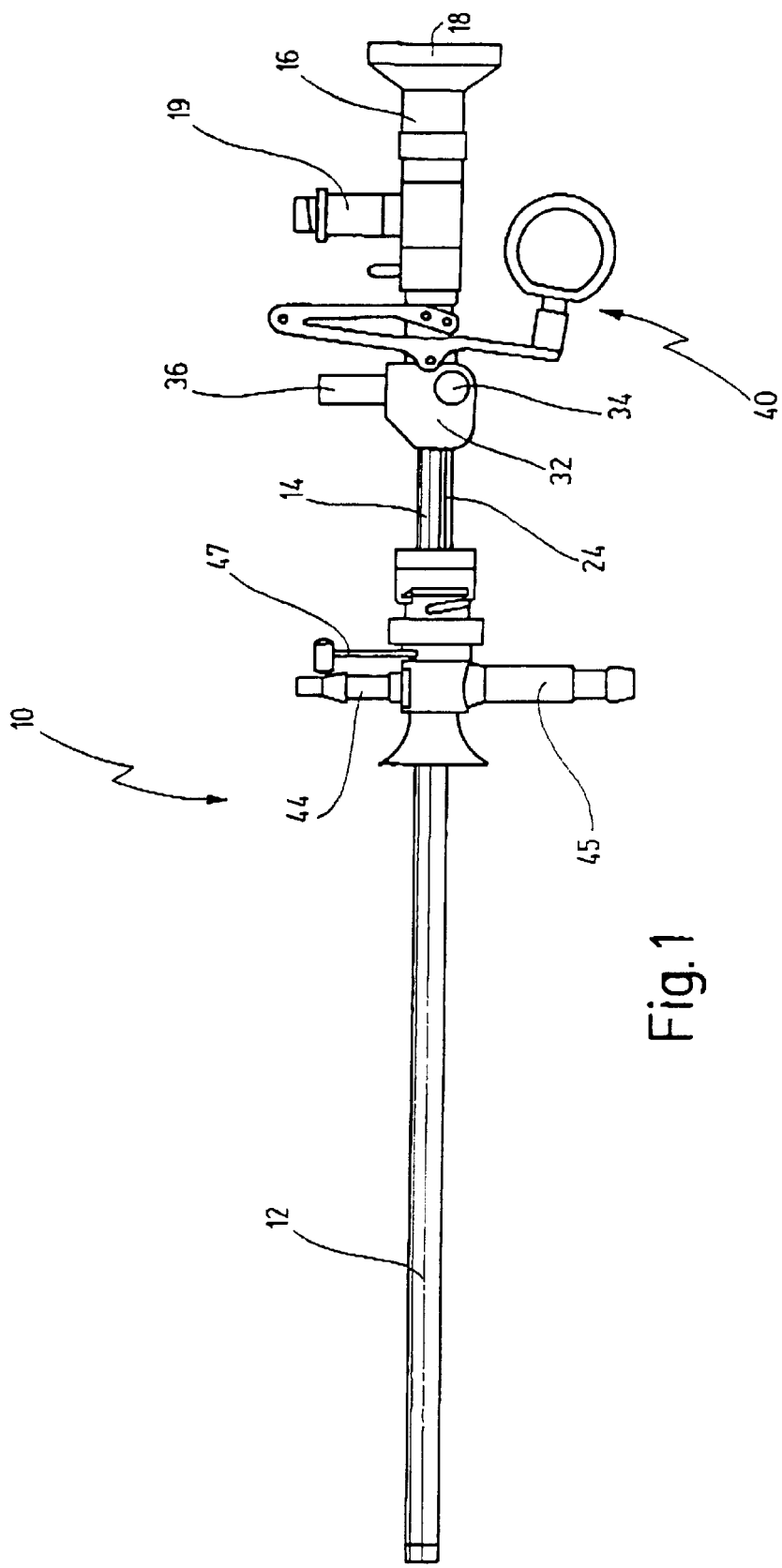
FIG. 1 shows a side view of an endoscopic instrument as a whole.

FIGS. 1 to 4 show an endoscopic instrument for medical purposes generally indicated with the numeral 10. In this embodiment, the instrument 10 is a resectoscope used in urology for minimally invasive removal of tissue in the bladder or prostate gland.

The invention is described in the following with reference to this medical instrument however, it can just as well be used in technical endoscopic instruments.

The instrument 10 comprises an elongated shaft 12. An endoscope optical system 14 is arranged in the shaft, which includes an ocular 16 with an eyepiece 18 at the proximal end. A light conductor connector 19 on the ocular 16 provides connection of an optical cable (not shown) to supply light into the endoscope optical system 14.

The endoscope optical system 14, more precisely the optical shaft, is shown in FIGS. 1 to 3 in which an imaging system is arranged, for example in the form of a relay lens arrangement and a light guiding system in the form of optical fibres, which communicate with the light conductor connector 19.

The endoscope optical system 14 comprises a distal front face 20 at its distal end, which represents the light emission or the light inlet side of the endoscope optical system 14. The front face 20 is formed by a cover glass which closes the shaft of the endoscope optical system 14 at the distal end. The endoscope optical system 14 represents a so-called forward view (0°) system by which the front face 20 is disposed perpendicular to the optical axis 21.

The endoscope optical system 14 is arranged in the shaft 12 to be stationary in its working position, wherein the distal front face 20 remains disposed in the shaft 12 itself and is located proximally behind a distal opening 22 of the shaft 12. The endoscope optical system 14 is removable from the shaft 12 when disassembling the instrument 10.

A working element 24 is also arranged in the shaft 12.

The working element 24 at its distal end comprises a tool 26 in the form of a high frequency (HF) electrode 28 used as a cutting electrode, which is formed at an angle with respect to the axial direction of the working element 24.

The remaining part of the working element 24 forms an electrode carrier 30 consisting of an insulating shaft, in which an electrical line (not shown) leads to the electrode 28.

As shown in FIG. 1, a proximal end of the working element 24 is connected in locking manner to a housing portion 32, where a locking knob 34 serves to release the working element 24 from the housing portion 32. An HF connector 36 is located on the housing portion 32 for connecting an HF cable (not shown) which is connected to an HF generator.

The working element 24 is axially movable back and forth as indicated by the double arrow 38 relative to the endoscope optical system 14, where an operating element 40 is provided for shifting the working element 24 as shown in FIG. 1, which is also connected to the axially movable housing portion 32.

The axial motion of the working element 24 is guided along the endoscope optical system 14 by a sleeve 42 (FIGS. 2 and 3) through which the endoscope optical system 14 passes. In FIG. 2, the working element 24 is shown in solid lines at its maximally retracted position, where the electrode 28 is disposed in front of the distal front face 20 of the endoscope optical system 14. The dashed line represents the maximal advanced position to the distal end of the working element 24.

The shaft 12, more precisely the interior of the shaft 12, also serves as supply for an irrigation fluid which is introduced into the shaft 12 at its proximal end through an irrigation connector 44 for connecting an irrigation tube (not shown). The irrigation fluid is passed through the interior of the shaft 12 to the distal end. The entire free inner cross-section of the shaft 12, apart from the endoscope optical system 14 and the working element 24, serve as an irrigation cross-section. The axial flow of the irrigation fluid in the shaft 12 is illustrated in FIG. 2 with arrows 46. The fluid is passed to the distal end opening 22 of the shaft and exits the shaft 12 into the operation area being treated.

In the present case, where the instrument is an HF instrument, the irrigation fluid has a low electric conductivity.

The front face 20 of the endoscope optical system 14 thus is disposed perpendicularly to the flow direction of the irrigation fluid. A suction connection 45 is arranged opposite the irrigation connector 44, to which a suction tube (not shown) can be connected to later suction off irrigation fluid out of the operation area. A switch 47 is provided to switch between irrigation and suctioning.

To avoid formation of a dead space in the flow directly in front of the distal front face 20 of the endoscope optical system 14, where blood, pieces of tissue or gas bubbles resulting from the high frequency treatment of the tissue can collect, flow-influencing means 48 are provided which cause the front face 20 or the space directly there before to be sufficiently irrigated with fluid during the operation to allow unobstructed visual control of the operation procedure.

The flow-influencing means 48 in the embodiment of FIGS. 1 to 4 comprise at least one flow element 50, which includes a surface 52 against which the fluid flows and which is arranged to be inclined or transverse to the flow direction indicated by the arrow 46. The surface 52 is configured to be flat.

The flow element 50 is provided on the working element 24 in the form of a rod, which is attached as an additional member to the working element 24, for example by soldering, welding, adhering, or clamping, so that it is also removable or can be adjusted in position.

The working element 24 comprises a forked section 54 in its distal region, which forms two legs 56, 58. The legs 56, 58 in the retracted position of the working position 24 shown by the solid lines in FIG. 2 run alongside the endoscope optical system 14. The legs 56, 58 carry the electrode 28 configured as a sling (FIG. 4) at their distal ends. The legs 56, 58 run together into a proximal unitary section 60 of the electrode carrier 30, which extends axially and outside of the axis of the endoscope optical system 14.

The working element 24 comprises a bend 62 between the forked section 54 and the unitary section 60 of the working element 24, which connects the forked section 54 to the unitary section 60, wherein the legs 56, 58 in the region of the bend 62 run together approximately in a V-shape. The bend 62 is also a part of the flow-influencing means 48.

The flow-influencing means 48 comprise a further flow element 64 apart from the mentioned flow element 50, wherein the flow element 50 is arranged on the leg 56 and the flow element 64 is arranged on the leg 58, namely each at the distal end of the bend.

Further flow elements 66, 68 are arranged at an axial spacing from the flow elements 50, 64 on the forked section 54 of the working element 24.

Apart from the flow elements 50, 64, 66, 68 illustrated in FIGS. 2 and 3, still further flow elements can be arranged axially and/or about the circumference of the working element 24, more precisely on the legs 56, 58 of the forked section 54.

The flow element 50, more precisely the surface 52 against which the irrigation fluid flows, represents an obstruction to flow in the form of an impact surface, which causes a swirling of the irrigation fluid directly in front of the front face 20 of the endoscope optical system, when the working element 24 is located in the position indicated by the dashed lines in FIG. 2 or is located in the working position shown in FIG. 3. The same effect is produced by a surface 70 of the flow element 64.

In the working position shown in FIG. 3, the bend 62 also represents a flow-influencing means 48, which leads to enhanced swirling of the irrigation fluid and therefore to an irrigation of the front face 20 of the endoscope optical system 14. The swirling effect can be increased by moving the working element 24 back and forth as indicated by the double arrow 38, whereby the flow conditions in the region of the distal front face 20 of the endoscope optical system 14 is also influenced, such that sufficient irrigation fluid is deflected in front of the front face 20.

When the working element 24 is retracted from the maximally distal position shown in FIG. 3 in the proximal direction to a position so that the flow elements 66, 68 lie axially in front of the front face 20, a flow-influence occurs due to these flow elements 66, 68 as described above.

Although the flow elements 50, 64, 66, 68 are formed as small rods attached to the working element 24, the flow-influence means can also be configured in the form of small plates, guide plates, projections or deflection blades or the like. Such flow elements as additional pieces can be removably or fixedly secured to the working element 24 or formed integrally with the working element 24. Flow elements can also be used having concave surfaces curved in the direction of an optic axis 21, against which the flushing fluid flows, so that the flow disrupting effect consists substantially of a change in flow direction rather than a swirling effect.

Furthermore, such flow elements can be arranged on the shaft 12 or on the endoscope optical system 14 in the region of the distal front face 20 to suitably affect the flushing fluid flow, so that contaminations in front of the front face 20 can be washed away.

In the embodiment of FIGS. 1 to 4, the working element 24 is adapted for removing tissue with high frequency power, where instead of a cutting electrode such as the electrode 28, a coagulation electrode can be present on the working element 24. However, the invention can also employ a working element 74 shown in FIG. 5, which has a purely mechanically acting tool 75 in the form of forceps jaws. The working element 74 also comprises flow influencing means 76 including one or more flow elements 78 to 84, which depending on the axial position of the working element 74 have the effect that the irrigation fluid reaches in front of the distal front face 20.

What is claimed is:

1. An endoscopic instrument, comprising a shaft, an endoscope optical system arranged in said shaft, said endoscope optical system having a distal front face, and a working element arranged in said shaft, wherein said shaft serves to supply an irrigation fluid into an operation or application area, wherein flow-influencing means are provided such that said irrigation fluid reaches in front of said front face of said endoscope optical system, and wherein said flow-influencing means are provided on said working element.

2. The instrument of claim 1, wherein said flow-influencing means are configured as flow obstructions which cause a swirling of said irrigation fluid in front of said front face of said endoscope optical system.

3. The instrument of claim 1, wherein said flow-influencing means are configured as flow deflection means, which generate a flow component along said front face of said endoscope optical system.

4. The instrument of claim 1, wherein said flow-influencing means comprise at least one flow element which comprises a surface, against which said irrigation fluid flows and which is inclined or runs transversely with respect to a flow direction of said irrigation fluid.

5. The instrument of claim 4, wherein said surface is flat or has a concave curvature directed to an axis of said endoscope optical system.

6. The instrument of claim 1, wherein said working element is axially shiftable relative to said endoscope optical system.

7. The instrument of claim 1, wherein said working element comprises a shaft with a mechanically acting tool.

8. An endoscopic instrument, comprising a shaft, an endoscope optical system arranged in said shaft, said endoscope optical system having a distal front face, and a working element arranged in said shaft, wherein said shaft serves to supply an irrigation fluid into an operation or application area, wherein flow-influencing means are provided such that said irrigation fluid reaches in front of said front face of said endoscope optical system, and wherein said flow-influencing means are provided on said working element and comprise several flow elements which are arranged axially distributed on said working element.

9. An endoscopic instrument, comprising a shaft, an endoscope optical system arranged in said shaft, said endoscope optical system having a distal front face, and a working element arranged in said shaft, wherein said shaft serves to supply an irrigation fluid into an operation or application area, wherein flow-influencing means are provided such that said irrigation fluid reaches in front of said front face of said endoscope optical system, and wherein said flow-influencing means are provided on said working element and comprise several flow elements which are circumferentially distributed on said working element.

10. An endoscopic instrument, comprising a shaft, an endoscope optical system arranged in said shaft, said endoscope optical system having a distal front face, and a working element arranged in said shaft, wherein said shaft serves to supply an irrigation fluid into an operation or application area, wherein flow-influencing means are provided such that said irrigation fluid reaches in front of said front face of said endoscope optical system, and wherein said flow-influencing means are provided on said working element and comprise several flow elements which are arranged axially distributed on said working element, wherein said working element comprises a forked section in a distal region, wherein two legs of said forked section run axially along the sides of said endoscope optical system and run together in a proximal unitary section, which extends axially adjacent to said endoscope optical system, and wherein said working element comprises a bend in the transmission region from said forked section to said unitary section, which lies axially in a region of said front face of said endoscope optical system in at least one axial working position of said working element.

11. An endoscopic instrument, comprising a shaft, an endoscope optical system arranged in said shaft, said endoscope optical system having a distal front face, and a working element arranged in said shaft, wherein said shaft serves to supply an irrigation fluid into an operation or application area, wherein flow-influencing means are provided such that said irrigation fluid reaches in front of said front face of said endoscope optical system, and wherein said flow-influencing means are provided on said working element, wherein said working element is an electrode carrier which carries an electrode supplyable with HF power.

* * * * *